United States Patent
Wei et al.

(10) Patent No.: US 11,754,523 B2
(45) Date of Patent: Sep. 12, 2023

(54) DETECTION DEVICE AND METHOD FOR CORONAVIRUS AND INFLUENZA VIRUS

(71) Applicant: Fudan University, Shanghai (CN)

(72) Inventors: Dacheng Wei, Shanghai (CN); Changhao Dai, Shanghai (CN); Banpeng Cao, Shanghai (CN); Xuejun Wang, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 17/925,832

(22) PCT Filed: Mar. 7, 2022

(86) PCT No.: PCT/CN2022/079465
§ 371 (c)(1),
(2) Date: Nov. 17, 2022

(87) PCT Pub. No.: WO2022/188725
PCT Pub. Date: Sep. 15, 2022

(65) Prior Publication Data
US 2023/0168224 A1    Jun. 1, 2023

(30) Foreign Application Priority Data
Mar. 10, 2021 (CN) .......................... 202110258434.1

(51) Int. Cl.
*G01N 27/414* (2006.01)

(52) U.S. Cl.
CPC ..... *G01N 27/4145* (2013.01); *G01N 27/4146* (2013.01)

(58) Field of Classification Search
None
See application file for complete search history.

(56) References Cited

U.S. PATENT DOCUMENTS

| 2008/0063566 A1 | 3/2008 | Matsumoto et al. |
| 2017/0059514 A1 | 3/2017 | Hoffman |
| 2021/0003528 A1 | 1/2021 | Esquivel-Upshaw et al. |

FOREIGN PATENT DOCUMENTS

| CN | 101051038 | 10/2007 |
| CN | 102841199 | 12/2012 |

(Continued)

OTHER PUBLICATIONS

Giwan Seo; et al., "Rapid Detection of COVID-19 Causative Virus (SARS-CoV-2) in Human Nasopharyngeal Swab Specimens Using Field-Effect Transistor-Based Biosensor," ACS Nano, vol. 14, No. 4, Apr. 2020, pp. 5135-5142.

(Continued)

*Primary Examiner* — J. Christopher Ball
(74) *Attorney, Agent, or Firm* — JCIPRNET

(57) ABSTRACT

The present application is related to a detection device and method for coronavirus and influenza virus. The device comprises a detection module (20), a signal processing circuit (30), a controller (40), a displayer (50), a digital-to-analog conversion circuit (60), and a clock (70). Noticeably, the detection module (20) comprises a sample cell, and a transistor sensor combination integrated in the sample cell and used for measuring different targets. The detection module (20) may comprise a sample cell array to realize simultaneous detection of a plurality of samples to be detected. The detection method comprises the following steps: adding a sample to be detected into a sample cell, reading an electrical signal response of each transistor sensor in the sample cell to judge whether the sample to be detected contains a virus to be detected or not. The present application belongs to the technical field of biological detection.

8 Claims, 7 Drawing Sheets

(56) References Cited

FOREIGN PATENT DOCUMENTS

| | | |
|---|---|---|
| CN | 106461586 | 2/2017 |
| CN | 111474365 | 7/2020 |
| CN | 111850168 | 10/2020 |
| CN | 211955219 | 11/2020 |
| CN | 113125544 | 7/2021 |
| WO | 2018085385 | 5/2018 |

OTHER PUBLICATIONS

Yanxiao Li; et al., "MXene—Graphene Field-Effect Transistor Sensing of Influenza Virus and SARS-CoV-2," ACS Omega, vol. 6, No. 10, Mar. 2021, pp. 6643-6653.

Guojun Ke ; et al., "An accurate, high-speed, portable bifunctional electrical detector for COVID-19," Sci China Mater, vol. 64 No 3, Mar. 2021, pp. 739-747.

Badriyah Alhalaili ; et al., "Nanobiosensors for the Detection of Novel Coronavirus 2019-nCoV and Other Pandemic/Epidemic Respiratory Viruses: A Review," Sensors (Basel), vol. 20 No 22, 6591, Nov. 2020, pp. 1-45.

Wenting Shao ; et al., "Rapid Detection of SARS-CoV-2 Antigens Using High-Purity Semiconducting Single-Walled Carbon Nanotube-Based Field-Effect Transistors," ACS Applied Materials & Interfaces, vol. 13, No. 8, Feb. 2021, pp. 10321-10327.

You-Ren Hsu ; et al., "Detection of Severe Acute Respiratory Syndrome (SARS) Coronavirus Nucleocapsid Protein Using AlGaN/GaN High Electron Mobility Transistors," ECS Transactions, vol. 50, No. 6, Oct. 2012, pp. 239-243.

Deniz Sadighbayan ; et al., "Biosensing based on field-effect transistors (FET): Recent progress and challenges," Trends in Analytical Chemistry, vol. 133, 116067, Dec. 2020, pp. 1-16.

"International Search Report (Form PCT/ISA/210) of PCT/CN2022/079465," dated May 31, 2022, with English translation thereof, pp. 1-6.

"Written Opinion of the International Searching Authority (Form PCT/ISA/237) of PCT/CN2022/079465," dated May 31, 2022, pp. 1-5.

DETECTION DEVICE AND METHOD FOR CORONAVIRUS AND INFLUENZA VIRUS

CROSS-REFERENCE TO RELATED APPLICATION

This application is a 371 of international application of PCT application serial no. PCT/CN2022/079465, filed on Mar. 7, 2022, which claims the priority benefit of China application no. 202110258434.1, filed on Mar. 10, 2021. The entirety of each of the above-mentioned patent applications is hereby incorporated by reference herein and made a part of this specification.

TECHNICAL FIELD

The present disclosure belongs to the technical field of biological detection and particularly relates to a detection device and method for a coronavirus and an influenza virus.

BACKGROUND ART

Novel coronaviruses and most influenza viruses belong to ribonucleic acid (RNA) viruses, and have a relatively high mutation speed and strong transmission. In a peak season of influenza pandemic, the detection difficulty is increased by a superimposed effect of novel coronaviruses and influenza viruses. Detection means of novel coronaviruses and influenza viruses at the present mainly comprise nucleic acid detection and kit: the nucleic acid detection aims at a nucleocapsid protein gene, an envelope protein gene or an open reading frame gene in novel coronaviruses, needs steps of extraction, amplification, detection, interpretation and the like, takes long time (at least 2 h), has high requirements on devices and operators, and even can generate false negative and the like; and the kit detection aims at antibodies generated in a subject, cannot reflect a current infection level, has poor sensitivity, cannot accurately distinguish novel coronaviruses and influenza viruses, and increases difficulties in epidemic prevention and treatment. Therefore, there is a need to develop an effective virus detection device for screening novel coronaviruses and influenza viruses.

A sensitive material has a large specific surface area and an atomic layer thickness, such sensitive material yields a real-time and sensitive response to a tiny external disturbance. A transistor sensor based on the sensitive material realizes sensitive detection at a level of femtomole per liter ($10^{-15}$ mol/L) and is used to detect viruses, cells, pathogens, gases, metal ions and the like. By combining a semiconductor process and a printed circuit technology, the transistor sensor can realize function integration and thus provides possibility for multi-target detection.

In a hybrid detection technology, the detection of the target is influenced by the abundant non-object, thus a virus detection device needs to adopt a method with higher sensitivity, better antifouling capability and higher detection accuracy. Therefore, the detection accuracy and sensitivity need further improvement.

SUMMARY OF THE INVENTION

In order to solve the problems of complex operation, long detection time, and low sensitivity of the current virus detection method in a large-scale screening, the present disclosure provides a detection device and method for a coronavirus and an influenza virus. The method has the shortest detection time for a coronavirus and an influenza virus of 1 minute and can be used for detecting a single sample, a hybrid sample, and a mixed sample, thus, holding potential social and economic value.

The objectives of the present disclosure are achieved by the following technical solutions.

In one aspect of the present disclosure, a detection device for coronavirus and influenza virus is provided and comprises:

A detection module, a signal processing circuit, a controller, a displayer, a digital-to-analog conversion circuit, and a clock, wherein input ends of the detection module are separately connected with an output end of the digital-to-analog conversion circuit and the clock; an output end of the detection module is connected with an input end of the signal processing circuit; an input end of the controller is connected with an output end of the signal processing circuit; and output ends of the controller are separately connected with an input end of the displayer, the digital-to-analog conversion circuit, and the clock.

Furthermore, the detection module comprises a sample cell, in which transistor sensor combinations are used for measuring different targets. The detection module contains a sample cell or an array of 3 to 256 sample cells to realize detection of one sample to be detected or a combination of 3 to 256 samples to be detected.

Furthermore, the transistor device comprises 2 to 12 transistor sensor units. Each transistor sensor unit is modified with different biorecognition molecules and is integrated in the same sample cell. Each transistor sensor unit comprises an insulating substrate, electrodes fabricated on the insulating substrate, a sensitive material located between the electrodes, and the biorecognition molecule anchored on the sensitive material. The sensitive material comprises graphene, molybdenum disulfide, tungsten disulfide, graphene oxide, a carbon nanotube, silicon, germanium, and an organic semiconductor thin film; and the biorecognition molecule comprises a molecule capable of specifically binding to different sites of a nucleic acid, a protein or antibody.

Furthermore, the digital-to-analog conversion circuit comprises a power supply voltage regulator circuit, a gate voltage control circuit, and a source-drain voltage control circuit; the signal processing circuit comprises a voltage reference, an operational amplifier, and an instrumentation amplifier, specifically comprises a reference power supply, a digital-to-analog converter, a differential operational amplifier, a microcontroller, a common-mode inductor, a linear voltage stabilizer, a chip active crystal oscillator, a chip passive crystal oscillator and the like; and the controller is connected with the displayer through a USB serial port, a Bluetooth and a Wi-Fi.

In another aspect of the present disclosure, a detection method for a coronavirus and an influenza virus is provided, and the detection method specifically comprises the following steps:

step 1, adding a testing sample into the sample cell of the detection module;

step 2, measuring an electrical signal response of all transistor sensor units in each sample cell of the detection module;

step 3, obtaining the number n of the transistor sensor units whose electrical signal response is greater than detection value A and the number m of the transistor sensor units whose electrical signal response is less than detection value B in each sample cell of the detection module; and step 4, determining whether the sample contains a corresponding virus to through the number n and m of the transistor sensor units.

Furthermore, the method specifically comprises the following steps:

adding a sample to be detected and obtaining an electrical signal response of a transistor sensor combination in a sample cell of the detection module;

calculating an electrical signal response $\Delta I_{detection}$ % of each transistor sensor unit;

comparing the $\Delta I_{detection}$ % of the transistor sensor unit with detection values A and B, if the $\Delta I_{detection}$ % is greater than the detection value A, determining that the number n of the transistor sensor units greater than the detection value A increases by 1; if the $\Delta I_{detection}$ % is less than the detection value B, determining that the number m of the transistor sensor units less than the detection value B increases by 1; and if the $\Delta I_{detection}$ % is between the detection values A and B, determining that the number n of the transistor sensor units greater than the detection value A is equal to 0 and the number m of the transistor sensor units less than the detection value B is equal to 0;

if the number n of the transistor sensor units is greater than or equal to 2, determining detected/positive, namely the sample to be detected contains a virus; if the number m of the transistor sensor units is greater than or equal to 1 and n is equal to 0, determining not detected/negative, namely the sample to be detected does not contain a virus; and if the number m and n of the transistor sensor units are other values, determining that the detection result is in a gray area and the detection needs to be repeated.

Furthermore, calculating the electrical signal response $\Delta I_{detection}$ % of the transistor sensor unit specifically comprises:

obtaining an initial current value $I_0$ of the transistor sensor unit after adding a negative control;

obtaining a measured current value $I_{detection}$ of the transistor sensor unit after adding a sample to be detected;

obtaining a current change value $\Delta I_{detection}$ ($\Delta I_{detection} = I_{detection} - I_0$) by subtracting the initial current value $I_0$ of the transistor sensor unit from the measured current value $I_{detection}$; and obtaining the electrical signal response $\Delta I_{detection}$ % ($\Delta I_{detection}\% = \Delta I_{detection}/I_0 \times 100\%$) of the transistor sensor unit by dividing the current change value $\Delta I_{detection}$ of the transistor sensor unit by the initial current value $I_0$.

Furthermore, the detection value A is equal to 3 times of an electrical signal response $\Delta I_{detection}$ % of a negative control; the detection value B is equal to the electrical signal response $\Delta I_{detection}$ % of the negative control. The negative control is prepared according to a type of a virus to be detected and a total positive rate of the virus to be detected in the population, and specifically comprises a virus preservation solution, artificial saliva, and healthy human serum.

Furthermore, the coronavirus comprises a coronavirus capable of infecting human beings in four genera of α, β, γ, and δ, and specifically comprises HCoV-229E, HCoV-OC43, SARS-CoV, HCoV-NL63, HCoV-HKU1, MERS-CoV, and SARS-CoV-2; and the influenza virus comprises an influenza A virus and an influenza B virus capable of infection human beings.

Furthermore, the sample to be detected comprises a single sample, a mixed sample, and a hybrid sample. The sample relates to a serum sample, a nasal swab sample, a pharyngeal swab sample, a respiratory tract aspirate, a bronchial lavage fluid, an alveolar lavage fluid, or a nasopharyngeal aspirate. When the serum sample is collected, the blood of a user to be detected is required to be held for several hours and then the serum is put into a sterile tube and packaged according to biosafety; and after the nasal swab sample, the pharyngeal swab sample, the respiratory tract aspirate, the bronchial lavage fluid, the alveolar lavage fluid, or the nasopharyngeal aspirate are collected, the collected samples are preserved using virus preservation tubes and packaged according to biosafety.

A processing method of the sample to be detected comprises:

(1) detection of nucleic acid contained in virus: after adding a nucleic acid extraction reagent to release virus RNA, inactivating the sample to be detected at a certain temperature; and (2) detection of protein contained in virus and corresponding antibody: inactivating the sample to be detected at a certain temperature.

The specific steps for collecting and processing a sample to be tested should refer to the "National Influenza Surveillance Technical Guidelines (2017 Edition)" of the Chinese Center for Disease Control and Prevention, and the "Technical Specifications for Detection of 10-in-1 Mixed Collection of Nucleic Acids of Novel Coronavirus" and "Technical Guidelines for Detection of Diluted Hybrid Sample for Novel Coronavirus Nucleic Acid Testing" of the National Health Commission of the People's Republic of China.

Compared with the prior art, the present disclosure has the following advantages:

In order to solve the problems of complex operation, long detection time, low sensitivity, and poor accuracy of the current virus detection technology, the present disclosure integrates multiple groups of transistor sensor units in the detection module and realizes detection of different target detection objects through biorecognition molecules targeting different binding sites of a virus. Based on the simultaneous detection of the different targets, the method significantly improves the detection accuracy and efficiency, and has the shortest detection time as short as 1 minute. Through a combination of multiple groups of the transistor sensor units and the biorecognition molecules in the detection module, the method can be used for detecting a single sample, a hybrid sample, and a mixed sample, and thus has potential social and economic value.

DETAILED DESCRIPTION OF THE EMBODIMENTS

The present disclosure will be further explained in detail below with reference to the accompanying drawings.

Figure 1:
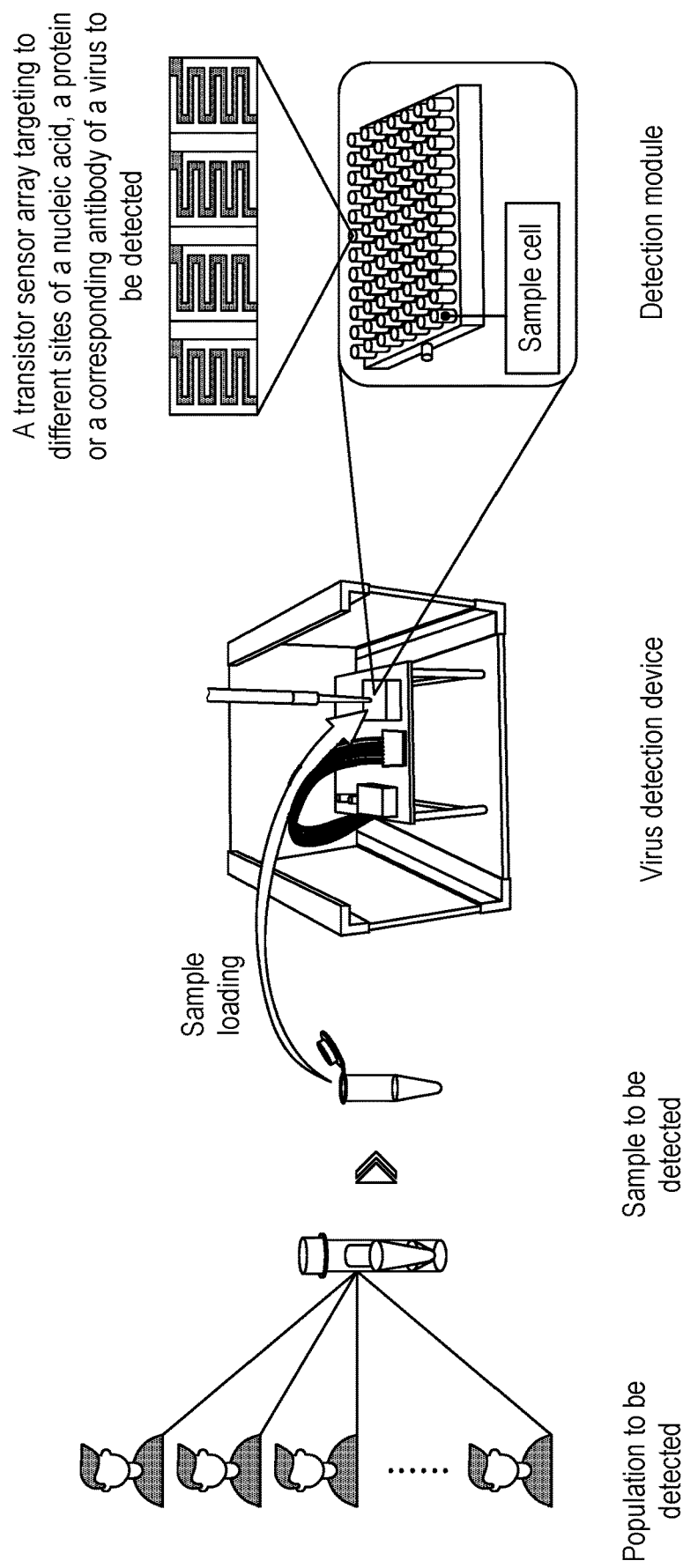
FIG. 1 is a schematic diagram of the operation flow of the detection device and method for a coronavirus and an influenza virus of the present disclosure.

FIG. 1 shows the operation flow of the detection device and method for a coronavirus and an influenza virus of the present disclosure:

adding a sample to be detected into a sample cell of a detection module;

obtaining an electrical signal response of all transistor sensor units in each sample cell of the detection module;

obtaining the number n of the transistor sensor units whose electrical signal response is greater than detection value A and the number m of the transistor sensor units whose electrical signal response is less than detection value B in each sample cell of the detection module; and determining whether the sample to be detected contains a corresponding virus through the number n and m of the transistor sensor units.

Furthermore, the sample to be detected comprises a single sample, a mixed sample, and a hybrid sample. The sample relates to a serum sample, a nasal swab sample, a pharyngeal swab sample, a respiratory tract aspirate, a bronchial lavage fluid, an alveolar lavage fluid, or a nasopharyngeal aspirate. Among them, when collecting serum samples, the blood of a user to be detected are required to be stood for several hours and then the serum is put into a sterile tube and packaged according to biosafety; and after the nasal swab sample, the pharyngeal swab sample, the respiratory tract aspirate, the bronchial lavage fluid, the alveolar lavage fluid, or the nasopharyngeal aspirate are collected, the collected samples are preserved using virus preservation tubes and packaged according to biosafety.

A processing method of the sample to be detected comprises:

(1) detection of nucleic acid contained in virus: after adding a nucleic acid extraction reagent to release virus RNA, inactivating the sample to be detected at 56° C. for 30 min; and (2) detection of protein contained in virus and corresponding antibody: inactivating the sample to be detected at 56° C. for 30 min.

The specific steps for collecting and processing a sample to be tested should refer to the "National Influenza Surveillance Technical Guidelines (2017 Edition)" of the Chinese Center for Disease Control and Prevention, and the "Technical Specifications for Detection of 10-in-1 Mixed Collection of Nucleic Acids of Novel Coronavirus" and "Technical Guidelines for Detection of Diluted Hybrid for Novel Coronavirus Nucleic Acid Testing" of the National Health Commission of the People's Republic of China.

Figure 2:
FIG. 2 is a step-by-step diagram of the detection method for a coronavirus and an influenza virus of the present disclosure.

Furthermore, whether the sample to be detected contains a corresponding virus is determined through the number n and m of the transistor sensor units. Specifically, the result is obtained by the steps shown in FIG. 2:

S10, adding a sample to be detected and obtaining an electrical signal response of a transistor sensor combination in a sample cell of a detection module;

S20, calculating an electrical signal response $\Delta I_{detection}$ % of each transistor sensor unit;

S30, determining whether the $\Delta I_{detection}$ % of the transistor sensor unit is greater than detection value A and determining whether the $\Delta I_{detection}$ % of the transistor sensor unit is less than detection value B;

S40, obtaining the number n of the transistor sensor units whose electrical signal response is greater than detection value A and the number m of the transistor sensor units whose electrical signal response is less than detection value B in each sample cell of the detection module;

S50, determining whether n is greater than or equal to 2 and determining whether n is equal to 0 and whether m is greater than or equal to 1; and S60, determining whether the sample to be detected is detected/positive, not detected/negative, or is in a gray area.

Furthermore, calculating the electrical signal response $\Delta I_{detection}$ % of the transistor sensor unit specifically comprises:

obtaining an initial current value $I_0$ of the transistor sensor unit after adding the negative control;

obtaining a measured current value $I_{detection}$ of the transistor sensor unit after adding a sample to be detected;

obtaining a current change value $\Delta I_{detection}$ ($\Delta I_{detection} = I_{detection} - I_0$) by subtracting the initial current value $I_0$ of the transistor sensor unit from the measured current value $I_{detection}$; and obtaining the electrical signal response $\Delta I_{detection}$ % ($\Delta I_{detection}\% = \Delta I_{detection}/I_0 \times 100\%$) of the transistor sensor unit by dividing the current change value $\Delta I_{detection}$ of the transistor sensor unit by the initial current value $I_0$.

Furthermore, the detection value A is equal to 3 times of an electrical signal response $\Delta I_{detection}$ % of a negative control; and the detection value B is equal to the electrical signal response $\Delta I_{detection}$ % of the negative control. The negative control is prepared by a detection personnel according to a type of a virus to be detected and a total positive rate of the virus to be detected in the population, and specifically comprises a virus preservation solution, artificial saliva and healthy human serum.

Figure 3:
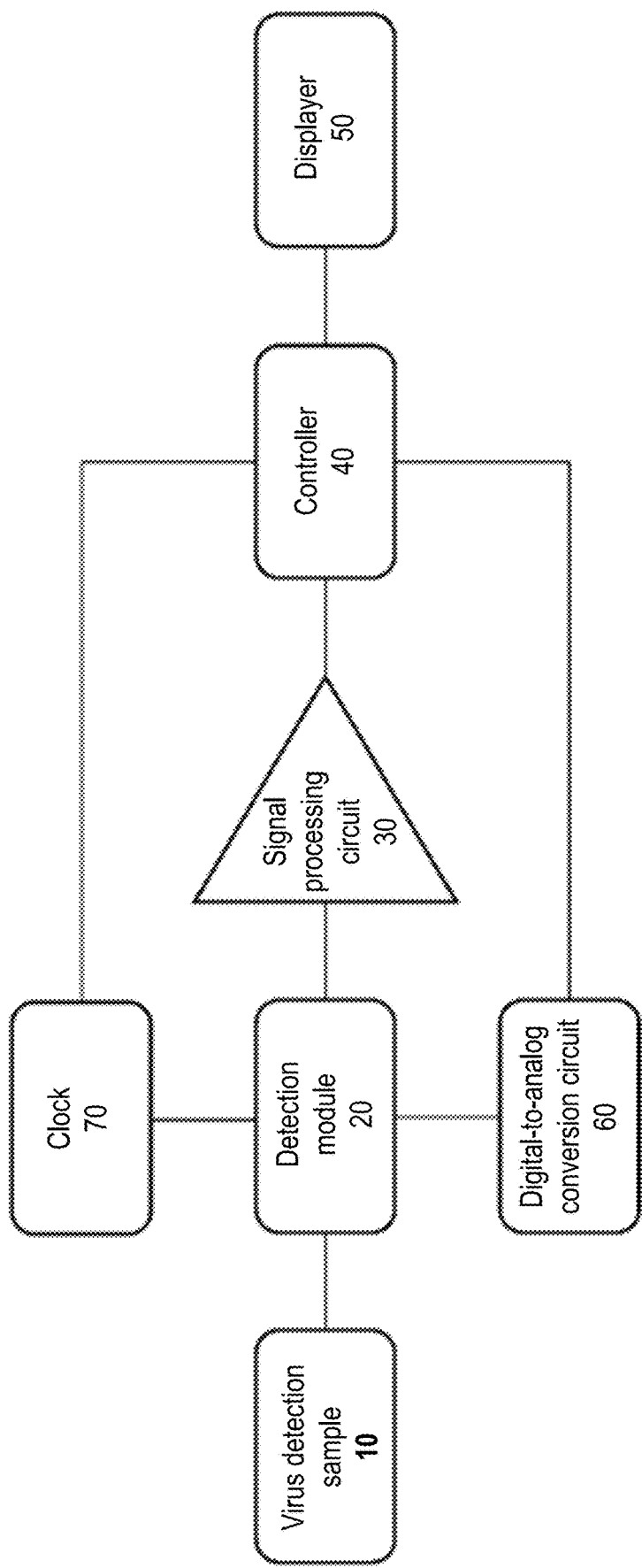
FIG. 3 is a connection diagram of the detection device for a coronavirus and an influenza virus of the present disclosure.

FIG. 3 is a connection diagram of the detection device for a coronavirus and an influenza virus of the present disclosure; and the detection device comprises a detection module 20, a signal processing circuit 30, a controller 40, a displayer 50, a digital-to-analog conversion circuit 60, and a clock 70. Input ends of the detection module 20 are connected with an output end of the digital-to-analog conversion circuit 60 and the clock 70; an output end of the detection module 20 is connected with an input end of the signal processing circuit 30; an output end of the signal processing circuit 30 is connected with an input end of the controller 40; and output ends of the controller 40 are connected with an input end of the displayer 50, the digital-to-analog conversion circuit 60, and the clock 70. Since specific recognition molecules are attached to a conductive channel of each transistor sensor unit in the detection module 20, different types and concentrations of virus detection samples can change the current carrier mobility of the sensitive material, thereby generating electrical signals. The signal processing circuit 30 collects current output by the detection module 20 and outputs the current to the controller to calculate to obtain a detection signal of a virus detection sample 10.

Figure 4:
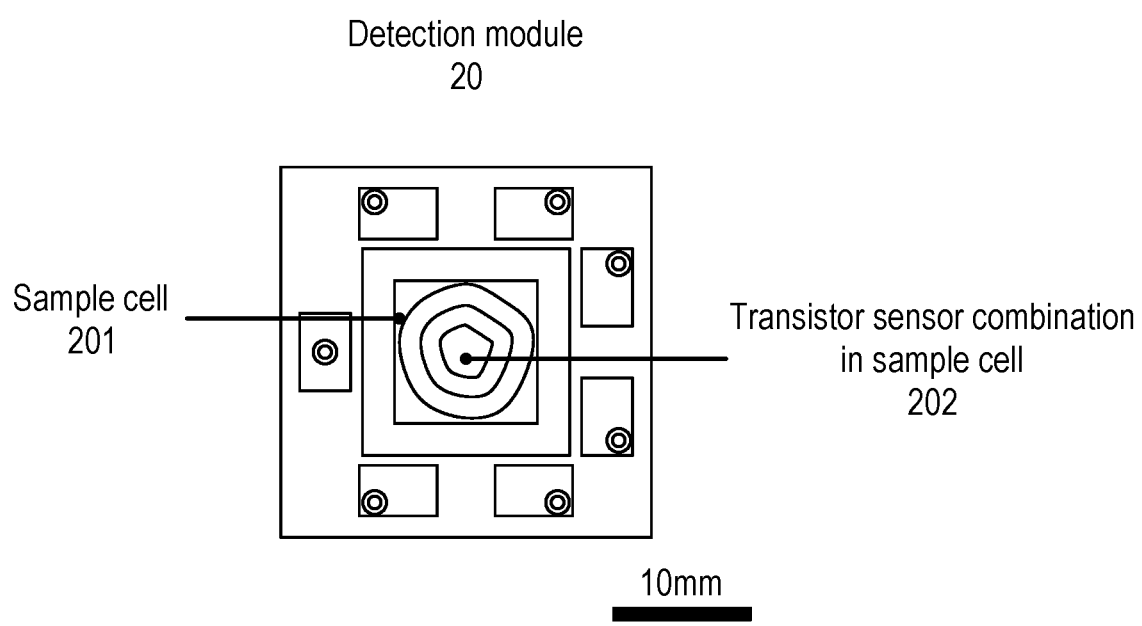
FIG. 4 shows the detection module of the detection device for a coronavirus and an influenza virus of the present disclosure.

Furthermore, the detection module comprises a sample cell 201 and a transistor sensor combination 202 integrated in the sample cell and used for measuring different targets. The detection module is as shown in FIG. 4. The detection module contains a sample cell or an array of 3 to 256 sample cells to realize detection of one sample to be detected or a combination of 3 to 256 samples to be detected.

Furthermore, the transistor sensor combination comprises 2 to 12 transistor sensor units. Each transistor sensor unit modifies different biorecognition molecules separately and is integrated in the same sample cell. Each transistor sensor unit comprises an insulating substrate, electrodes arranged on the insulating substrate, a sensitive material arranged on the insulating substrate and located between the electrodes, and the biorecognition molecule anchored on the sensitive material. The sensitive material comprises graphene, molybdenum disulfide, tungsten disulfide, graphene oxide, a carbon nanotube, silicon, germanium, and an organic semiconductor thin film; and the biorecognition molecule comprises a molecule capable of specifically binding to different sites of a nucleic acid, a protein or a corresponding antibody of a virus to be detected.

Figure 5:
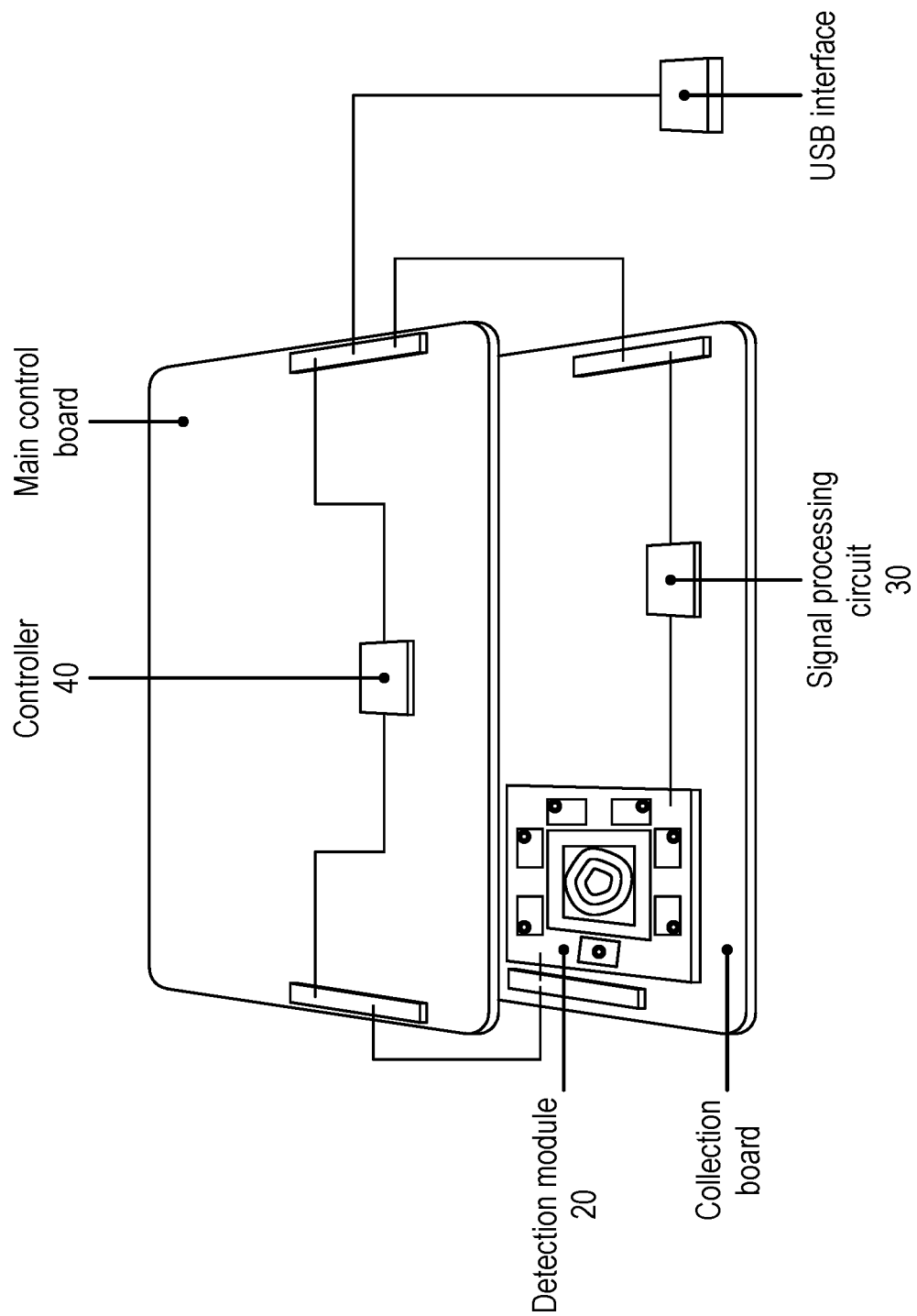
FIG. 5 shows the detection device for a coronavirus and an influenza virus of the present disclosure.

Furthermore, according to Table 1, site 1 of a main control board and site 2 of a collection board are connected to obtain the virus detection device (FIG. 5) with a test function; and then the virus detection device is connected to a notebook computer through a USB connecting line.

TABLE 1

Wiring table of detection device for coronavirus and influenza virus of the present disclosure

| Name | Site 1 | Name | Site 2 |
|---|---|---|---|
| Main control board | AP4 | Collection board | VG |
| Main control board | AN4 | Collection board | GND |
| Main control board | AP3 | Collection board | VD3 |
| Main control board | AN3 | Collection board | GND |
| Main control board | AP2 | Collection board | VD2 |
| Main control board | AN2 | Collection board | GND |
| Main control board | AP1 | Collection board | VD1 |
| Main control board | AN1 | Collection board | GND |
| Main control board | AGND | Collection board | GND |
| Main control board | DAC4 | Collection board | VGPK |
| Main control board | DAC3 | Collection board | VGDC |
| Main control board | DAC2 | Collection board | MODE |
| Main control board | DAC1 | Collection board | VGIT |
| Main control board | DAC8 | Collection board | EN |
| Main control board | DAC7 | Collection board | VD3 |
| Main control board | DAC6 | Collection board | VD2 |
| Main control board | DAC5 | Collection board | VD1 |
| Main control board | DGND | USB interface | GND |
| Main control board | Tx | USB interface | Rxd |
| Main control board | Rx | USB interface | Txd |

Example 1

The example presented a detection result of a single sample of a novel coronavirus and specifically comprised the following steps:

Step 1, a detection module 20 for a novel coronavirus was prepared: processing of a transistor sensor combination comprised the following seven steps:

(a) a photoresist was spin-coated on a single-polished silicon oxide wafer (including 300 nm $SiO_2$ in an upper layer and 500 μm P-type doped Si in a lower layer) and an electrode pattern was exposed and developed;

(b) the electrode pattern was subjected to evaporation to obtain metal electrodes (5 nm chromium and 50 nm gold), wherein the electrodes comprised a source electrode and a drain electrode, the source electrode was a current input end and the drain electrode was a current output end;

(c) 8 wt. % of polymethyl methacrylate (PMMA) was spin-coated on graphene grown on a metal substrate, the graphene/PMMA film was electrochemically transferred to a Si/$SiO_2$ substrate with the metal electrodes, the film-coated substrate was connected between the source electrode and the drain electrode, soaked in acetone for 2 h and then washed with isopropanol/deionized water, and graphene was etched into a specific shape by photolithography to obtain a device to be modified;

(d) the device to be modified was annealed at a current of 500 μA for 10 min;

(e) a connection molecule was modified in a graphene channel region (non-metallic electrode component) on the device to be modified, and an example was: after graphene was soaked in $5 \times 10^{-3}$ mol/L of 1-pyrenebutyric acid N-hydroxysuccinimide ester solution for 2 h, the graphene was washed with absolute ethanol and deionized water;

(f) after the graphene was soaked in a novel coronavirus specific antibody solution for 6 h, the graphene was washed with a 1×phosphate buffered saline solution; and (g) after the graphene was soaked in $200 \times 10^{-3}$ mol/L of an ethanolamine solution for 2 h, the graphene was washed with absolute ethanol and a phosphate buffered saline solution to obtain the detection module.

Step 2, a virus detection device with a test function was obtained by the connection according to the steps described in the specific embodiments.

Step 3, a novel coronavirus sample to be detected was prepared:

(a) bilateral pharyngeal tonsils and a posterior pharyngeal wall were wiped with 2 plastic-rod swabs with polypropylene fiber tips at the same time, the swab tips were soaked in a tube containing 3 mL of a virus preservation solution (or an isotonic saline solution, a tissue culture solution and a phosphate buffer solution), tails of the swabs were discarded, the tube cap was tightened, and the sample was packaged according to biosafety requirements;

(b) 0.5 mL of the sample to be detected in the sampling tube was taken, placed in a centrifuge tube, and thoroughly mixed (shaken on a shaker for 30 s) to obtain a hybrid sample, and the sample was packaged according to biosafety requirements; and (c) the sample to be detected was inactivated at 56° C. for 30 min.

Step 4, a novel coronavirus sample to be detected was detected:

(a) 100 μL of a negative control (virus preservation solution) was added to a sample cell of the detection module, and an output voltage of the virus detection device was set to enable a fluctuation range of the electrical signal response of the transistor sensor combination to be less than ±0.3%; and detection value A was set to ±0.9% and detection value B was set to ±0.3%;

(b) the negative control was taken out, 100 μL of the sample to be detected was added in a sample cell of the detection module, and the electrical signal response of the transistor sensor combination in a sample cell of the detection module was obtained;

(c) the number n of the transistor sensor units whose electrical signal response was greater than detection value A and the number m of the transistor sensor units whose electrical signal response was less than detection value B in each sample cell of the detection module were obtained according to the steps of the specific embodiments; and (d) whether the sample to be detected was detected/positive, not detected/negative, or is in a gray area was determined.

Figure 6:
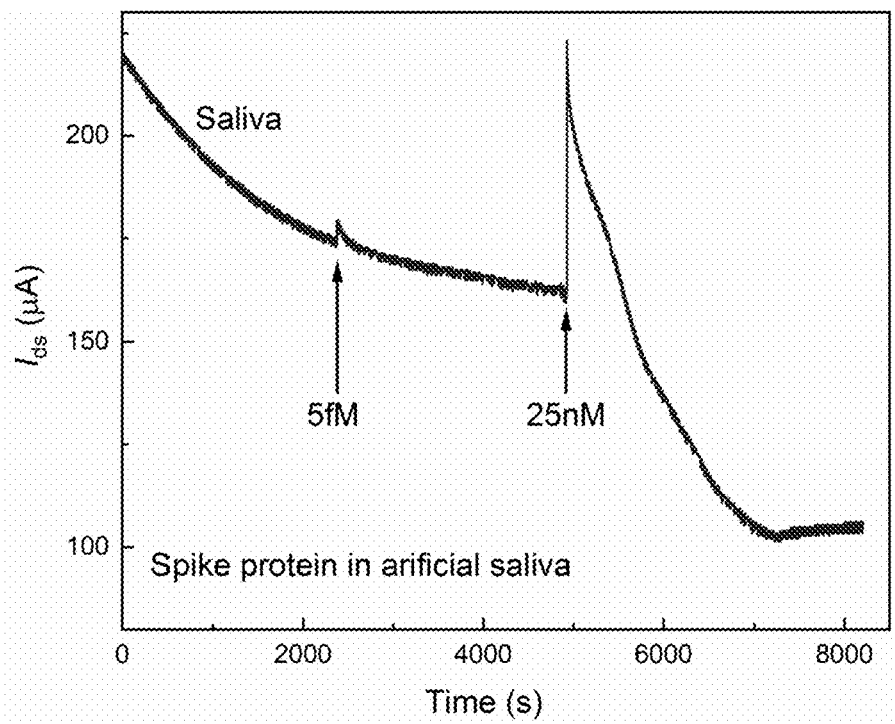
FIG. 6 is the detection result of the single sample of the detection device for a coronavirus and an influenza virus in example 1 of the present disclosure.

FIG. 6 was the electrical signal response generated by a transistor sensor unit 203 in the example: after a sample to be detected containing $2.5 \times 10^{-8}$ mol/L of a spike protein of a novel coronavirus, the electrical signal response of the transistor sensor unit was close to 25% and greater than detection value A, that is, the number n of the transistor sensor units whose electrical signal response was greater than detection value A was equal to 1.

Example 2

Detection was performed according to the method of the specific embodiments. The differences between the example and example 1 were:

(1) A sample to be detected used in the example was collected in accordance with the "Technical Specifications for Detection of 10-in-1 Mixed Collection of Nucleic Acids of Novel Coronavirus" of the National Health Commission of the People's Republic of China and was directly added to a sample cell of a virus detection device without pretreatment, wherein, M1 is a mixed sample of throat swabs of 10 healthy people; and M3 is a "mock positive mixed sample" obtained by adding $5 \times 10^{-12}$ mol/L of a spike protein of a novel coronavirus to M1; and (2) 100 μL of a negative control (virus preservation solution) was added to a sample cell of a detection module, and an output voltage of the virus detection device was set to enable a fluctuation range of the electrical signal response of the transistor sensor combination to be less than ±0.5%; and detection value A was set to ±1.5% and detection value B was set to ±0.5%.

Figure 7:
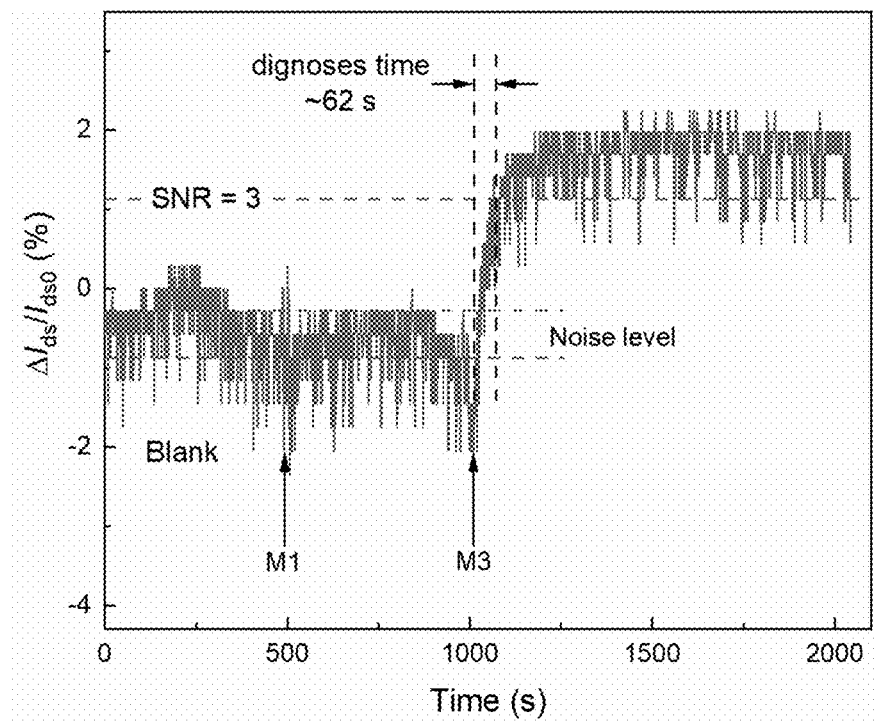
FIG. 7 is the detection result of the mixed sample of the detection device for a coronavirus and an influenza virus in example 2 of the present disclosure.

FIG. 7 was the detection result of the mixed sample of the example: after M1 was added, the number n of the transistor sensor units whose electrical signal response was greater than detection value A was equal to 0 and the number m of the transistor sensor units whose electrical signal response was less than detection value B was equal to 2, and thus M1 was determined to be not detected/negative, that is, did not contain a virus. After M3 was added, the number n of the transistor sensor units whose electrical signal response was greater than detection value A was equal to equal to 2, and thus M3 was determined to be detected/positive, that is, contained a virus.

Example 3

Detection was performed according to the method of the specific embodiments. The differences between the example and example 1 were:

(1) A sample to be detected used in the example was a hybrid sample and directly added to a sample cell of a virus detection device without pretreatment, wherein, M1 is a mixed sample of throat swabs of 10 healthy people; and M2, M3, M4, M5, and M6 were "mock positive hybrid samples" obtained by adding a certain concentration of a spike protein of a novel coronavirus to M1; and after calibration, M2 contains $0.5 \times 10^{-12}$ mol/L of the spike protein of a novel coronavirus; M3 contains $5 \times 10^{-12}$ mol/L of the spike protein of a novel coronavirus; M4 contains $50 \times 10^{-12}$ mol/L of the spike protein of a novel coronavirus; M5 contains $500 \times 10^{-12}$ mol/L of the spike protein of a novel coronavirus; and M6 contains $50 \times 10^{-9}$ mol/L of the spike protein of a novel coronavirus; and (2) 100 μL of a negative control (virus preservation solution) was added to a sample cell of a detection module, and an output voltage of the virus detection device was set to enable a fluctuation range of the electrical signal response of the transistor sensor combination to be less than ±0.13%; and detection value A was set to ±0.39% and detection value B was set to ±0.13%.

Figure 8:
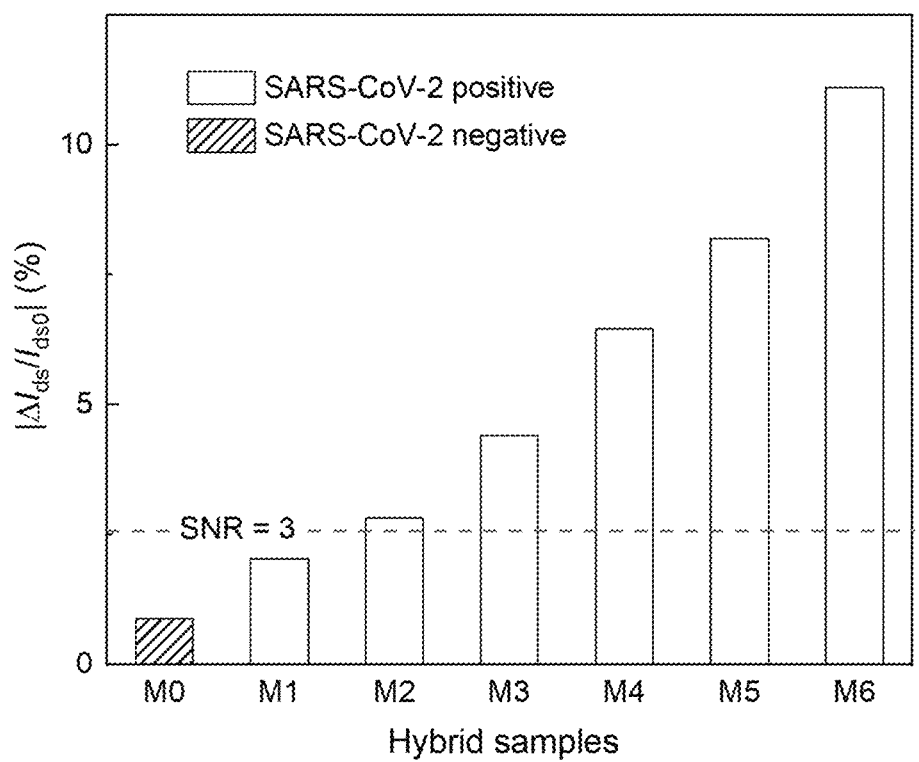
FIG. 8 is the statistical detection result of the hybrid sample of the detection device for a coronavirus and an influenza virus in example 3 of the present disclosure.

FIG. 8 was the statistical detection result of the hybrid samples in the example: after M1 was added, the electrical signal response $\Delta I_{detection}$ % of the transistor sensor unit was 0.27%, between the detection value A and the detection value B, and in a gray area; and after M2 to M5 were added, the electrical signal response $\Delta I_{detection}$ % of the transistor sensor unit was all greater than the detection value A, the number n of the transistor sensor units whose electrical signal response greater than the detection value A was calculated to be equal to 3, and thus M2 to M5 were detected/positive, that is, contained a novel coronavirus.

The above description of the examples is intended to facilitate a person of ordinary skill in the art to understand and use the present disclosure. Obviously, a person skilled in the art can easily make various modifications to these examples, and apply a general principle described herein to other examples without creative efforts. Therefore, the present disclosure is not limited to the above examples. All improvements and modifications made by a person skilled in the art according to implication of the present disclosure without departing from the spirit of the present disclosure should fall within the protection scope of the present disclosure.

What is claimed is:

1. A detection method for a coronavirus and an influenza virus, wherein a detection device for a coronavirus and an influenza virus is used for detection,
   the detection device for a coronavirus and an influenza virus comprises a detection module, a signal processing circuit, a controller, a displayer, a digital-to-analog conversion circuit, and a clock, wherein input ends of the detection module are separately connected with an output end of the digital-to-analog conversion circuit and the clock; an output end of the detection module is connected with an input end of the signal processing circuit; an input end of the controller is connected with an output end of the signal processing circuit; and output ends of the controller are separately connected with an input end of the displayer, the digital-to-analog conversion circuit, and the clock;
   the detection module comprises a sample cell, and transistor sensor combination integrated in the sample cell and used for measuring different targets, the transistor sensor combination comprises a plurality of transistor sensor units, and each of the transistor sensor units modify different biorecognition molecules separately and is integrated in the same sample cell;
   the detection method specifically comprises the following steps:
   step 1, adding a sample to be detected into the sample cell of the detection module;
   step 2, obtaining an electrical signal response of all transistor sensor units in each of the sample cell of the detection module;
   step 3, obtaining the number n of the transistor sensor units whose electrical signal response is greater than detection value A and the number m of the transistor sensor units whose electrical signal response is less than detection value B in each of the sample cell of the detection module; and
   step 4, determining whether the sample to be detected contains a corresponding virus to be detected through the number n and m of the transistor sensor units;
   wherein, in step 3, the detection value A is equal to 3 times of an electrical signal response $\Delta I_{detection}$ % of a negative control; the detection value B is equal to the electrical signal response $\Delta I_{detection}$ % of the negative control, wherein, in step 4, specifically comprising the following steps:
adding a sample to be detected and obtaining an electrical signal response of a transistor sensor combination in a sample cell of the detection module;
obtaining an electrical signal response $\Delta I_{detection}$ % of each of the transistor sensor units;
comparing the $\Delta I_{detection}$ % of the transistor sensor unit with the detection values A and B, if the $\Delta I_{detection}$ % is greater than the detection value A, determining that the number n of the transistor sensor units greater than the detection value A increases by 1; if the $\Delta I_{detection}$ % is less than the detection value B, determining that the number m of the transistor sensor units less than the detection value B increases by 1; and if the $\Delta I_{detection}$ % is between the detection values A and B, determining that the number n of the transistor sensor units greater than the detection value A equal to 0 and the number m of the transistor sensor units less than the detection value B equal to 0;
if the number n of the transistor sensor units is greater than or equal to 2, determining detected/positive, namely the sample to be detected contains a virus to be detected; if the number m of the transistor sensor units is greater than or equal to 1 and n is equal to 0, determining not detected/negative, namely the sample to be detected does not contain a virus to be detected; and if the numbers m and n of the transistor sensor units are other values, determining that the detection result is in a gray area and the detection needs to be repeated;
wherein process of calculating the electrical signal response $\Delta I_{detection}$ % of the transistor sensor unit specifically comprises:
obtaining an initial current value $I_0$ of the transistor sensor unit after adding the negative control;
obtaining a measured current value $I_{detection}$ of the transistor sensor unit after adding a sample to be detected;
obtaining a current change value $\Delta I_{detection}$ ($\Delta I_{detection} = I_{detection} - I_0$) by subtracting the initial current value $I_0$ of the transistor sensor unit from the measured current value $I_{detection}$; and
obtaining the electrical signal response $\Delta I_{detection}$ % ($\Delta I_{detection}\% = \Delta I_{detection}/I_0 \times 100\%$) of the transistor sensor unit by dividing the current change value $\Delta I_{detection}$ of the transistor sensor unit by the initial current value $I_0$.

2. The detection method for a coronavirus and an influenza virus according to claim 1, wherein each of the transistor sensor unit comprises an insulating substrate, electrodes arranged on the insulating substrate, a sensitive material arranged on the insulating substrate and located between the electrodes, and the biorecognition molecules are anchored on the sensitive material.

3. The detection method for a coronavirus and an influenza virus according to claim 2, wherein the sensitive material comprises graphene, molybdenum disulfide, tungsten disulfide, graphene oxide, a carbon nanotube, silicon, germanium, and an organic semiconductor thin film; and
the biorecognition molecules comprise a molecule capable of specifically binding to different sites of a nucleic acid, a protein or a corresponding antibody of a virus to be detected.

4. The detection method for a coronavirus and an influenza virus according to claim 1, wherein the detection module contains a sample cell or an array of 3 to 256 sample cells; and
the transistor sensor combination comprises 2 to 12 transistor sensor units.

5. The detection method for a coronavirus and an influenza virus according to claim 1, wherein the digital-to-analog conversion circuit comprises a power supply voltage regulator circuit, a gate voltage control circuit, and a source-drain voltage control circuit; and
the signal processing circuit comprises a voltage reference, an operational amplifier, and an instrumentation amplifier.

6. The detection method for a coronavirus and an influenza virus according to claim 1, wherein the coronavirus comprises a coronavirus capable of infecting human beings in four genera of α, β, γ, and δ, and specifically comprises HCoV-229E, HCoV-OC43, SARS-COV, HCoV-NL63, HCoV-HKU1, MERS-COV, and SARS-COV-2; and
the influenza virus comprises an influenza A virus, an influenza B virus and an influenza C virus.

7. The detection method for a coronavirus and an influenza virus according to claim 1, wherein the sample to be detected comprises a single sample, a mixed sample, and a hybrid sample, and a processing method of the sample to be detected comprises:
(1) detection of nucleic acid contained in virus: after adding a nucleic acid extraction reagent to release virus RNA, inactivating the sample to be detected at a certain temperature; and
(2) detection of protein contained in virus and corresponding antibody: inactivating the sample to be detected at a certain temperature.

8. The detection method for a coronavirus and an influenza virus according to claim 1, wherein the electrical signal response $\Delta I_{detection}$ % of the negative control is prepared by a detection personnel according to a type of a virus to be detected and a total positive rate of the virus to be detected in a population, and specifically comprises a virus preservation solution, artificial saliva, and healthy human serum.

* * * * *